United States Patent
Su

(10) Patent No.: US 6,287,545 B1
(45) Date of Patent: *Sep. 11, 2001

(54) HAIR CONDITIONER COMPOSITIONS HAVING IMPROVED FREEZING AND FREEZE-THAW STABILITY

(75) Inventor: Dean Terng-Tzong Su, Princeton Junction, NJ (US)

(73) Assignee: Colgate-Palmolive Company, New York, NY (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/548,886

(22) Filed: Dec. 1, 1995

Related U.S. Application Data

(63) Continuation-in-part of application No. 08/359,094, filed on Dec. 19, 1994, now abandoned.

(51) Int. Cl.[7] .................................................. A61K 7/06
(52) U.S. Cl. ................. 424/70.12; 424/70.1; 424/70.11; 424/70.19
(58) Field of Search ............................. 424/70.19, 70.31, 424/70.1, 70.11, 70.12

(56) References Cited

U.S. PATENT DOCUMENTS

| | | | |
|---|---|---|---|
| 4,605,018 | 8/1986 | de la Guardia et al. | 132/7 |
| 4,711,776 * | 12/1987 | Suzuki | 424/70 |
| 4,765,975 | 8/1988 | Iovanni et al. | 424/70 |
| 4,859,456 | 8/1989 | Marschner | 424/47 |
| 4,886,660 | 12/1989 | Patel et al. | 424/70 |
| 4,911,919 | 3/1990 | Patel et al. | 424/70 |
| 4,954,335 | 9/1990 | Janchipraponvej | 424/70 |
| 4,963,348 | 10/1990 | Bolich, Jr. et al. | 424/71 |
| 4,976,956 | 12/1990 | Noe | 424/70 |
| 5,002,761 | 3/1991 | Mueller et al. | 424/70 |
| 5,015,415 | 5/1991 | Goze et al. | 252/547 |
| 5,019,377 | 5/1991 | Torgerson | 424/70 |
| 5,082,660 | 1/1992 | Ounanian et al. | 424/63 |
| 5,204,105 | 4/1993 | Mausner | 424/401 |
| 5,213,793 | 5/1993 | Moses et al. | 424/70 |
| 5,215,759 | 6/1993 | Mausner | 424/489 |
| 5,248,445 | 9/1993 | Rizvi et al. | 252/174.15 |
| 5,254,336 | 10/1993 | Hoshowski et al. | 424/70 |
| 5,288,481 | 2/1994 | Ounanian et al. | 424/63 |
| 5,306,486 | 4/1994 | McCook et al. | 424/59 |
| 5,320,834 | 6/1994 | Ounanian et al. | 424/63 |
| 5,336,432 | 8/1994 | Petchul et al. | 252/186.28 |

* cited by examiner

Primary Examiner—Thurman K. Page
Assistant Examiner—Brian K. Seidleck
(74) Attorney, Agent, or Firm—Rosemary M. Miano; Bernard F. Crowe

(57) ABSTRACT

A system for enhancing the freezing and freeze-thaw stability of hair conditioning compositions has been developed which comprises incorporating therein a combination of low HLB (from about 2.0 to about 9.0) and high (from about 10.0 to about 19.0) HLB ethoxylated branched-chain fatty alcohol ethers and/or esters as freeze-thaw stabilizers while maintaining the pH of said emulsion in a range of about 2.0 to about 5.5.

16 Claims, No Drawings

HAIR CONDITIONER COMPOSITIONS HAVING IMPROVED FREEZING AND FREEZE-THAW STABILITY

This is a continuation-in-part of U.S. Ser. No. 08/359,094 filed Dec. 19, 1994 now abandoned.

BACKGROUND OF THE INVENTION

1. Field of the Invention

This invention relates to hair conditioner compositions which aid in the managing of human hair. More particularly it pertains to compositions which promote hair detangling and fly away and in addition exhibit good freeze-thaw stability.

2. Description of the Related Art

U.S. Pat. No. 4,374,825 discloses hair conditioning compositions in the form of an emulsion comprising a volatile agent, a nonionic, water soluble thickening agent, a cationic hair conditioning agent, and water.

U.S. Pat. No. 4,726,945 describes a stable hair rinse composition consisting essentially of distearyl or ditallow quaternary compound, a $C_7$–$C_{17}$ alkamido amine, propylene glycol, mineral oil, a $C_8$–$C_{18}$ alkanol and cyclomethicone in an aqueous vehicle.

U.S. Pat. No. 4,911,919 claims a stable hair straightening conditioner consisting essentially of a nonionic water-soluble cellulose polymer, polyvinyl pyrrolidone, a di-$C_{10}$–$C_{22}$ alkyl di-$C_1$–$C_3$ alkyl quaternary compound, a $C_8$–$C_{18}$ alkylamido $C_2$–$C_3$ alkyl di-$C_1$–$C_2$ alkyl amine, propylene glycol, mineral oil, a $C_8$–$C_{18}$ alkanol and cyclomethicone in an aqueous vehicle.

U.S. Pat. No. 4,954,335 teaches a method of imparting improved conditioning properties to hair comprising treating the hair with a clear conditioning composition comprising a quaternary ammonium compound, such as, dicetyldimonium chloride; an amidoamine compound; a volatile conditioning agent, such as, a volatile hydrocarbon compound or a volatile silicone compound, like cyclomethicone; a solubilizing nonionic surfactant, like lauryl pyrrolidone; and a polyhydric compound, such as, a glycol, a triol or a polyol, like hexylene glycol.

It is an object of this invention to improve the freeze-thaw stability of current hair conditioners which comprise aqueous emulsions of quaternary compounds, unctuous compounds and surfactant compounds.

Other objects will become apparent to those skilled in the art upon a further reading of the specification.

SUMMARY OF THE INVENTION

An improvement in the freeze-thaw stability of hair conditioners in the form of aqueous emulsions which contain combinations of quaternary ammonium salts, unctuous materials—particularly fatty alcohols that serve as conditioning and viscosity agents, surfactants or emulsifiers, and protective colloids or thickening compounds has been made which comprises incorporating therein a combination of high and low HLB ethoxylated branched-chain fatty alcohol ethers or esters as stabilizers, such as isoceteth-20 and isosteareth-2 or dipropylene glycol isoceteth-20 acetate and propylene glycol isoceteth-3 acetate, while maintaining a pH of about 2.0–5.5.

DESCRIPTION OF THE INVENTION

Hair conditioners formulated with fatty alcohols as conditioning and as primary emulsification and viscosity agents do not normally age well when they are subjected to the freeze-thaw cycles above. Since the fatty alcohols form liquid crystals (spherical or laminar) and entrap water in between the double layers, the water is released when the liquid crystal structures are destroyed by freezing. The undesirable formation of coarse gels is accompanied by significant increases in viscosity. Therefore viscosity measurements of the freeze-thaw samples serves to demonstrate the presence or absence of satisfactory hair conditioning compositions. Satisfactory samples do not gel or evince viscosity changes. In some samples a slight water separation may occur but this is not permanent, disappearing when a plastic bottle container is squeezed causing the water to mix back into the conditioner composition. This phenomenon is therefore not to be interpreted as failing a freeze-thaw test. The Brookfield Viscometer was used for these measurements with various spindles and spindle speeds.

Stability tests were conducted for the hair conditioner compositions in glass or plastic containers at varying temperatures of 49° C., 43° C., 38° C., 4° C., and –18° C.(freezing). Aging the test samples at these five temperatures is done independently from 3 cycles of freeze and thaw aging, viz., –18° C. (24 hours)→25° C. (24 hours)→18° C. (24 hours)→25° C.→–18° C. (24 hours)→25° C. (24 hours). All the aged products were evaluated at 25° C. after completing aging at each condition. The products made by this invention did not have problems after aging at temperatures of 4° C. and above. The hair conditioners provided through this invention remain extremely smooth after three cycles of freeze and thaw with no evidence of water separation.

It has now been found that the freeze-thaw stability of hair conditioner aqueous emulsions containing combinations of quaternary ammonium salts, unctuous materials, surfactants or emulsifiers, and protective colloids or thickening compounds can be improved by incorporating therein a combination of high and low HLB ethoxylated branched-chain fatty alcohol ethers or esters as stabilizers, such as isoceteth-20 and isosteareth-2 or dipropylene glycol isoceteth-20 acetate and propylene glycol isoceteth-3 acetate, while maintaining a pH of about 2.0–5.5.

In a broad sense the stabilizers are poly(oxyalkylene) glycol derivatives produced by the oxyalkylation of a branched-chain fatty alcohol starter with a 1,2-epoxide (e.g. ethylene oxide), which may be followed by further oxyalkylation with another 1,2-epoxide (e.g. 1,2 propylene glycol). The resulting alkyl ether may be terminated with a lower aliphatic acid.

Preferred low HLB stabilizers are those with HLB values of about 2.0 to about 9.0, obtained from oxyalkylation of branched-chain fatty alcohols, such as isocetyl alcohol and isostearyl alcohol, with up to eight moles of ethylene oxide and/or 1,2-propylene oxide. A preferred low HLB stabilizer is isosteareth-2, which is synthesized by ethoxylating isostearyl alcohol with two moles of ethylene oxide. It is available as Arosurf 66 2-E from Sherex Chemical Co. Another preferred low HLB stabilizer is propylene glycol isoceteth-3 acetate, which is synthesized by oxyalkylating isocetyl alcohol with one mole of 1,2-propylene glycol followed by with 3 moles of ethylene oxide and terminated with acetic acid. It is available as Hetester PHA from Bernel Chemical Co.

Preferred high HLB stabilizers are those with HLB values of about 10.0 to about 19.0, obtained from oxyalkylation of branched-chain fatty alcohols, such as isocetyl alcohol and isostearyl alcohol, with more than nine moles of ethylene oxide. A preferred high HLB stabilizer is isoceteth-20, which is synthesized by ethoxylating isocetyl alcohol with twenty moles of ethylene oxide. It is available as Arlasolve 200L from ICI Chemical Co. Another preferred high HLB stabilizer is dipropylene glycol isoceteth-20 acetate, which is synthesized by oxyalkylating isocetyl alcohol with two moles of 1,2-propylene glycol followed by with 20 moles of ethylene oxide and terminated with acetic acid, it is available as Cupl PIC from Bernel Chemical Co. These oxyalkylated branched-chain fatty alcohol ethers and esters are used herein in a range of about 0.01%–3% with a preferred range being from about 0.1–1%. These ethers and esters can be incorporated alone, but preferably they are incorporated as a combination of one low HLB and one high HLB compound. It is apparent to those skilled in the art that the branched-chain fatty alcohols are not confined to isocetyl alcohol and isostearyl alcohol and the ethers and esters include their derivatives which are derived from them.

Both mineral and organic acids can be used to maintain the claimed hair conditioners in a pH range of about 2.0 to about 5.5 and preferably about 3.0 to about 4.5. pH values of about 4 are achieved by the addition of about 0.01–2.0% and preferably about 0.01–1.0% of such hydroxy aliphatic acids as lactic acid, citric acid, itaconic acid, tartaric acid, ascorbic acid, and the like some of which can impart skin or scalp conditioning properties to these hair conditioners. However the invention is not limited to alpha-hydroxy acids.

The hair conditioning agents of the prior art usually contain long chain mono-, di- or even tri-higher alkyl quaternary ammonium compounds, such as cetyl trimonium chloride (cetyl trimethyl ammonium chloride), dicetyldimonium chloride (dicetyl dimethyl ammonium chloride), tricetylmonium chloride (tricetyl methyl ammonium chloride) or other long chain dialkyl ($C_{10}$–$C_{22}$) quaternary salts. Commonly, these cationic quaternary ammonium salts have the formula:

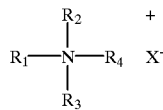

wherein $R_1$, $R_2$, $R_3$ and $R_4$ each alkyl groups or hydrogen with the proviso that at least one is higher alkyl and X is an anion, such as chloride, bromide or methyl sulfate. $R_1$ and $R_2$ can also be hydroxyalkyl monovalent radicals. Other representative quaternary salts include: steapyrium chloride, stearalkonium chloride, stearalkonium hectorite, stearamidopropalkonium chloride, steartrimonium chloride, stearyl hydroxyethylimidonium chloride, distearyl dimethyl ammonium chloride, dilauryl dimethyl ammonium chloride, di-hydrogenated tallow dimethyl ammonium chloride, dihexadecyl dimethyl ammonium chloride, ditetradecyl diethyl ammonium chloride, dicetyl dimethyl ammonium chloride, didicosyl dipropyl ammonium bromide, and dieicosyl diethyl ammonium methyl sulfate, and the like. These are usually present in a range of about 0.1–5% and preferably in a range of about 0.3–3%.

Various unctuous compounds used in the prior art hair conditioners include such diverse ingredients as, fatty alcohols, such as cetyl alcohol, stearyl alcohol, and the like; mineral oil, synthetic hydrocarbons such as isododecane, isohexadecane, silicones, and the like; fatty acid esters, and the like. Fatty alcohols can be present in a range of about 1–10% and preferably in a range of about 3–6%. Mineral oils or synthetic hydrocarbons can be present in a range of about 0.1–5% and preferably in a range of about 0.1–2.0%. Silicones, such as dimethicone (non-volatile) or cyclomethicone (volatile) and the like can be present in a range of about 0.1–5% and preferably in a range of about 0.1–2.0%.

Humectants including alkylene and polyalkylene glycols and triols including glycerol can be incorporated at levels of about 0.1–5% and preferably of about 0.1–2.0%.

Surfactants/emulsifiers are those that provide various functions such as improving stability at elevated temperatures, improving product texture/consistency as well as other aesthetic properties. Examples of surfactants/emulsifiers include anionic surfactants such as sodium cetearyl sulfate and the like, and alkyl phosphates as well as alkyl ether phosphates; amphoterics and betaines such as cocoamphoglycinate, cocoamidopropyl betaine and the like; and nonionics such as ethoxylated and/or propoxylated fatty alcohols and fatty esters, alkylamidopropylamines and the like.

Examples of protective colloids/thickeners include cellulose derivatives as, for example, methyl cellulose, hydroxyethyl cellulose, hydroxyalkyl methyl cellulose such as hydroxypropyl methylcellulose, sodium carboxymethyl cellulose, and the like.

Polycationic polymers known as "polyquaterniums" may also be incorporated in these compositions as supplemental hair conditioning agents at concentrations of about 0.01% to about 3.0% but preferably from about 0.1% to about 1.0%. Suitable polymers include the polymer of dimethyl diallyl ammonium chloride, which is known as Polyquaternium 6, a designation of the Cosmetic, Toiletry and Fragrance Association (CTFA) which is published in the CTFA International Cosmetic Ingredient Dictionary and is sold as Merquat 100 by Calgon; the polymeric quaternary ammonium salt consisting of acrylamide and dimethyl diallyl ammonium chloride monomers, which is known as Polyquaternium 7, and which is sold as Merquat 550 by Calgon; the polymeric quaternary ammonium salts of hydroxyethyl cellulose reacted with a trimethyl ammonium substituted epoxide, which are known as Polyquaternium 10, and which are sold as UCARE Polymer JR's by Amerchol; the quaternary ammonium polymers formed by the reaction of diethyl sulfate and a copolymer of vinyl pyrrolidone and dimethyl aminoethylmethacrylate, which are known as Polyquaternium 11, and which are sold as Gafquats by ISP; and the copolymers of hydroxyethylcellulose and diallyldimethyl ammonium chloride which are known as Polyquaternium 4, and which are sold as Celquats by National Starch, and the other known polyquaternium polymers useful as hair conditioning agents.

Other optional components can be used exemplified by dyes, perfumes, opacifiers, pearlescent aids, buffers, preservatives, antioxidants, and the like.

The invention is further described in the examples which follow. All parts and percentages are by weight unless otherwise specified.

The components listed below were blended into a creamy lotion using a sweep mixer by heating part A and part B to 80° C. in separate containers followed by adding the oil phase to the water phase while mixing at a suitable speed. A white lotion formed as soon as the two parts were mixed together. After mixing for ten minutes at 80° C., part C was added slowly to the white lotion, which brought the temperature down, resulting in a creamier lotion. The lotion was then cooled while mixing at medium speed to a temperature most appropriate for fragrance and preservative additions. The conditioner lotion may also be made by combining all the water together without retaining part C and by following the same procedure as described above. Other mixers such as a homo-mixer, turbine mixer, or Lightnin mixer may also be used.

Viscosity measurements were made with a Brookfield viscometer, RVT model, using spindle #5 at 10 rpm speed or spindle #4 at 20 rpm speed. Good examples evince viscosities after three freeze and thaw cycles. Failed examples were terminated after one cycle because of hardened and grainy lotion. Viscosities are considered good if they do not greatly change either way from the stabilized viscosity (i.e. the viscosity after 48 hours). While viscosities may change in the range of about 20% to about 25%, the important consideration is the lack of graininess of the lotion (i.e. the smoothness of its texture).

EXAMPLE 1

| Components | Weight % |
|---|---|
| Part A | |
| Deionized Water | 50.422 |
| Citric acid, anhydrous | 0.210 |
| Distearyl dimonium chloride | 0.750 |
| Hydroxyethyl cellulose | 0.200 |
| Propylene glycol | 0.500 |
| Part B | |
| Stearyl alcohol | 1.000 |
| Cetyl alcohol | 3.400 |
| Stearamidopropyl dimethylamine | 1.000 |
| Mineral oil | 0.550 |
| Cyclomethicone | 0.750 |
| Dimethicone, 60,000 cs | 0.750 |
| Part C | |
| Deionized water | 40.000 |
| Fragrance | 0.400 |
| Preservative | 0.068 |
| total | 100.000 |

EXAMPLE 2

| Components | Weight % |
|---|---|
| Part A | |
| Deionized Water | 51.172 |
| Citric acid, anhydrous | 0.210 |
| Distearyl dimonium chloride | 0.750 |
| Hydroxyethyl cellulose | 0.200 |
| Propylene glycol | 0.500 |
| Part B | |
| Stearyl alcohol | 1.000 |
| Cetyl alcohol | 3.400 |
| Stearamidopropyl dimethylamine | 1.000 |
| Mineral oil | 0.550 |
| Cyclomethicone | 0.750 |
| Part C | |
| Deionized water | 40.000 |
| Fragrance | 0.400 |
| Preservative | 0.068 |
| total | 100.000 |

EXAMPLE 3

| Components | Weight % |
|---|---|
| Part A | |
| Deionized Water | 50.822 |
| Citric acid, anhydrous | 0.210 |
| Distearyl dimonium chloride | 0.750 |
| Hydroxyethyl cellulose | 0.200 |
| Propylene glycol | 0.500 |
| Part B | |
| Stearyl alcohol | 1.000 |
| Cetyl alcohol | 3.000 |
| Stearamidopropyl dimethylamine | 1.000 |
| Mineral oil | 0.550 |
| Cyclomethicone | 0.750 |
| Dimethicone, 60,000 cs | 0.750 |
| Part C | |
| Deionized water | 40.000 |
| Fragrance | 0.400 |
| Preservative | 0.068 |
| total | 100.000 |

EXAMPLE 4

| Components | Weight % |
|---|---|
| Part A | |
| Deionized Water | 54.710 |
| Citric acid, anhydrous | 0.220 |
| Distearyl dimonium chloride | 0.750 |
| Hydroxyethyl cellulose | 0.200 |
| Propylene glycol | 0.500 |
| Part B | |
| Stearyl alcohol | 1.000 |
| Cetyl alcohol | 3.000 |
| Stearamidopropyl dimethylamine | 1.000 |
| Mineral oil | 0.500 |
| Cyclomethicone | 0.250 |
| Polysorbate 80 & cetyl acetate & acetylated lanolin alcohol | 0.250 |
| PEG-25 hydrogenated castor oil | 0.250 |
| Part C | |
| Deionized water | 36.520 |
| Fragrance | 0.350 |
| Preservative | 0.500 |
| total | 100.000 |

EXAMPLE 5

| Components | Weight % |
|---|---|
| Part A | |
| Deionized Water | 54.710 |
| Citric acid, anhydrous | 0.100 |
| Distearyl dimonium chloride | 1.000 |
| Hydroxyethyl cellulose | 0.200 |
| Propylene glycol | 0.500 |

-continued

| Components | Weight % |
|---|---|
| Part B | |
| Stearyl alcohol | 1.000 |
| Cetyl alcohol | 3.000 |
| Stearamidopropyl dimethylamine | 0.500 |
| Mineral oil | 0.500 |
| Cyclomethicone | 0.250 |
| Polysorbate 80 & cetyl acetate & acetylated lanolin alcohol | 0.250 |
| Ceteareth-10 | 0.350 |
| Ceteareth-5 | 0.350 |
| Part C | |
| Deionized water | 36.440 |
| Fragrance | 0.350 |
| Preservative | 0.500 |
| total | 100.000 |

EXAMPLE 6

| Components | Weight % |
|---|---|
| Part A | |
| Deionized Water | 50.222 |
| Citric acid, anhydrous | 0.110 |
| Distearyl dimonium chloride | 1.250 |
| Hydroxyethyl cellulose | 0.200 |
| Propylene glycol | 0.500 |
| Part B | |
| Stearyl alcohol | 0.800 |
| Cetyl alcohol | 3.200 |
| Stearamidopropyl dimethylamine | 0.500 |
| Mineral oil | 0.500 |
| Cyclomethicone | 1.250 |
| Dimethicone, 60,000 cs | 0.500 |
| Polysorbate 80 | 0.500 |
| Part C | |
| Deionized water | 40.000 |
| Fragrance | 0.400 |
| Preservative | 0.068 |
| total | 100.000 |

EXAMPLE 7

| Components | Weight % |
|---|---|
| Part A | |
| Deionized Water | 88.927 |
| Citric acid, anhydrous | 0.155 |
| Distearyl dimonium chloride | 1.750 |
| Hydroxyethyl cellulose | 0.200 |
| Propylene glycol | 0.500 |
| Part B | |
| Stearyl alcohol | 1.000 |
| Cetyl alcohol | 3.000 |
| Stearamidopropyl dimethylamine | 0.750 |
| Mineral oil | 0.750 |
| Cyclomethicone | 1.000 |
| Dimethicone, 60,000 cs | 0.750 |
| Glyceryl monostearate | 0.350 |

-continued

| Components | Weight % |
|---|---|
| PEG-15 hydrogenated castor oil | 0.400 |
| Fragrance | 0.400 |
| Preservative | 0.068 |
| total | 100.000 |

EXAMPLE 8

| Components | Weight % |
|---|---|
| Part A | |
| Deionized Water | 89.012 |
| Citric acid, anhydrous | 0.120 |
| Distearyl dimonium chloride | 1.750 |
| Hydroxyethyl cellulose | 0.200 |
| Propylene glycol | 0.500 |
| Part B | |
| Stearyl alcohol | 1.000 |
| Cetyl alcohol | 3.200 |
| Stearamidopropyl dimethylamine | 0.500 |
| Mineral oil | 0.750 |
| Cyclomethicone | 1.000 |
| Dimethicone, 60,000 cs | 0.750 |
| Ceteareth-10 | 0.400 |
| Ceteareth-5 | 0.350 |
| Fragrance | 0.400 |
| Preservative | 0.068 |
| total | 100.000 |

EXAMPLE 9

| Components | Weight % |
|---|---|
| Part A | |
| Deionized Water | 89.402 |
| Citric acid, anhydrous | 0.080 |
| Distearyl dimonium chloride | 1.250 |
| Hydroxyethyl cellulose | 0.250 |
| Propylene glycol | 0.500 |
| Lactic acid, 85% | 0.300 |
| Part B | |
| Stearyl alcohol | 1.500 |
| Cetyl alcohol | 3.000 |
| Stearamidopropyl dimethylamine | 1.000 |
| Mineral oil | 0.550 |
| Cyclomethicone | 0.750 |
| Dimethicone, 60,000 cs | 0.550 |
| Dipropylene glycol isoceteth-20 acetate | 0.150 |
| Propylene glycol isoceteth-3 acetate | 0.150 |
| Fragrance | 0.500 |
| Preservative | 0.068 |
| total | 100.000 |

EXAMPLE 10

Example 10

| Components | Weight % |
|---|---|
| Part A | |
| Deionized Water | 49.612 |
| Citric acid, anhydrous | 0.150 |
| Distearyl dimonium chloride | 1.250 |
| Hydroxyethyl cellulose | 0.350 |
| Propylene glycol | 0.500 |
| Lactic acid, 85% | 0.120 |
| Part B | |
| Stearyl alcohol | 1.400 |
| Cetyl alcohol | 3.000 |
| Stearamidopropyl dimethylamine | 1.000 |
| Mineral oil | 0.550 |
| Cyclomethicone | 0.750 |
| Dimethicone, 60,000 cs | 0.550 |
| Dipropylene glycol isoceteth-20 acetate | 0.100 |
| Propylene glycol isoceteth-3 acetate | 0.100 |
| Part C | |
| Deionized water | 40.000 |
| Fragrance | 0.500 |
| Preservative | 0.068 |
| total | 100.000 |

EXAMPLE 11

Example 11

| Components | Weight % |
|---|---|
| Part A | |
| Deionized Water | 90.160 |
| Citric acid, anhydrous | 0.120 |
| Distearyl dimonium chloride | 1.500 |
| Hydroxyethyl cellulose | 0.200 |
| Propylene glycol | 0.500 |
| Polyquaternium-16 | 0.250 |
| Part B | |
| Stearyl alcohol | 1.000 |
| Cetyl alcohol | 3.400 |
| Stearamidopropyl dimethylamine | 0.500 |
| Mineral oil | 0.500 |
| Cyclomethicone | 0.500 |
| Dimethicone, 60,000 cs | 0.500 |
| Isosteareth-2 | 0.200 |
| Isoceteth-20 | 0.200 |
| Part C | |
| Deionized water | 40.000 |
| Fragrance | 0.400 |
| Preservative | 0.070 |
| total | 100.000 |

EXAMPLE 12

Example 12

| Components | Weight % |
|---|---|
| Part A | |
| Deionized Water | 90.530 |
| Citric acid, anhydrous | 0.000 |
| Distearyl dimonium chloride | 1.250 |
| Hydroxyethyl cellulose | 0.200 |
| Propylene glycol | 0.500 |
| Lactic acid, 85% | 0.150 |
| Polyquaternium-16 | 0.200 |
| Part B | |
| Stearyl alcohol | 1.450 |
| Cetyl alcohol | 3.050 |
| Stearamidopropyl dimethylamine | 0.350 |
| Mineral oil | 0.550 |
| Cyclomethicone | 0.550 |
| Dimethicone, 60,000 cs | 0.550 |
| Dipropylene glycol isoceteth-20 acetate | 0.100 |
| Propylene glycol isoceteth-3 acetate | 0.100 |
| Fragrance | 0.400 |
| Preservative | 0.070 |
| total | 100.000 |

EXAMPLE 13

Example 13

| Components | Weight % |
|---|---|
| Part A | |
| Deionized water | 90.225 |
| Citric acid | 0.005 |
| Cetrimonium chloride - 25% | 2.600 |
| Hydroxyethyl cellulose | 0.200 |
| Propylene glycol | 0.500 |
| Part B | |
| Stearyl alcohol | 1.000 |
| Cetyl alcohol | 3.500 |
| Mineral oil | 0.500 |
| Dimethicone, 350 cs | 0.500 |
| Dimethicone, 60,000 cs | 0.500 |
| Fragrance | 0.400 |
| Preservative | 0.070 |
| total | 100.000 |

EXAMPLE 14

Example 14

| Components | Weight % |
|---|---|
| Part A | |
| Deionized water | 89.747 |
| Citric acid | 0.003 |
| Cetrimonium chloride - 25% | 2.600 |
| Propylene glycol | 0.500 |
| Part B | |
| Stearyl alcohol | 1.000 |
| Cetyl alcohol | 3.500 |

Example 14

| Components | Weight % |
| --- | --- |
| Mineral oil | 1.000 |
| Dimethicone, 350 cs | 0.250 |
| Dimethicone, 60,000 cs | 0.250 |
| Isosteareth-2 | 0.200 |
| Isoceteth-20 | 0.200 |
| Fragrance | 0.400 |
| Preservative | 0.350 |
| total | 100.000 |

EXAMPLE 15

Example 15

| Components | Weight % |
| --- | --- |
| Part A | |
| Deionized water | 89.445 |
| Citric acid | 0.005 |
| Cetrimonium chloride - 25% | 2.600 |
| Propylene glycol | 0.500 |
| Hydroxyethyl cellulose | 0.200 |
| Part B | |
| Stearyl alcohol | 1.000 |
| Cetyl alcohol | 3.500 |
| Mineral oil | 0.500 |
| Dimethicone, 350 cs | 0.500 |
| Dimethicone, 60,000 cs | 0.500 |
| Isosteareth-2 | 0.200 |
| Isoceteth-20 | 0.200 |
| Fragrance | 0.500 |
| Preservative | 0.350 |
| total | 100.000 |

EXAMPLE 16

Example 16

| Components | Weight % |
| --- | --- |
| Part A | |
| Deionized water | 89.245 |
| Citric acid | 0.005 |
| Cetrimonium chloride - 25% | 2.600 |
| Propylene glycol | 0.500 |
| Hydroxyethyl cellulose | 0.200 |
| Part B | |
| Stearyl alcohol | 1.150 |
| Cetyl alcohol | 3.150 |
| Mineral Oil | 0.500 |
| Dimethicone, 350 cs | 0.750 |
| Dimethicone, 60,000 cs | 0.750 |
| Isosteareth-2 | 0.200 |
| Isoceteth-20 | 0.200 |
| Fragrance | 0.400 |
| Preservative | 0.350 |
| total | 100.000 |

Example 1 had a pH of 4.03 and an initial viscosity of 11800 cps. However the lotion became hard and grainy and so was taken through only one freeze-thaw cycle.

Example 2 had a pH of 4.05 and an initial viscosity of 9600 cps. Since the lotion became hard and grainy, it was taken through only one freeze-thaw cycle.

Example 3 had a pH of 4.16 and an initial viscosity of 8640 cps. After 22 hours it exhibited a viscosity of 10440 cps. After one freeze-thaw cycle, the lotion hardened with water on the top surface. The viscosity was 25360 cps at this point.

Example 4 had a pH of 4.29 and an initial viscosity of 13640 cps. The viscosity after one freeze-thaw cycle was 17800 cps at which time the lotion was observed to be slightly grainy with water on the top surface.

Example 5 had a pH of 4.71 and an initial viscosity of 14680 cps. The lotion was harder and grainy and separated after one freeze-thaw cycle.

Example 6 had a pH of 4.30 and an initial viscosity of 6080 cps. The viscosity after 24 hours was 7660 cps. After one freeze-thaw cycle the lotion was grainy with water on the top.

Example 7 had a pH of 4.45 and an initial viscosity of 4360 cps. After one freeze-thaw cycle the lotion was hard and grainy.

Example 8 had a pH of 3.86 and an initial viscosity of 2200 cps. After one freeze-thaw cycle the lotion was very hard.

Example 9 had a pH of 3.78 and an initial viscosity of 12400 cps. The lotion remained smooth with a nice texture after three freeze-thaw cycles at which point the viscosity was 8880 cps.

Example 10 had a pH of 4.10 and an initial viscosity of 12520 cps. The lotion successfully passed through three freeze-thaw cycles maintaining its smooth texture. The viscosity at this point was 11440 cps.

Example 11 had a pH of 4.06 and an initial viscosity of 6160 cps. The lotion maintained its smooth texture through three freeze-thaw cycles having a viscosity of 5770 cps at the end.

Example 12 had a pH of 3.85 and an initial viscosity of 3310 cps. The lotion maintained its nice smooth texture through three freeze-thaw cycles ending with a viscosity of 5480 cps.

Example 13 had a pH of 3.36 and an initial viscosity of 2240 cps. The lotion hardened with water on the top after one freeze-thaw cycle at which time the viscosity was 4060 cps.

Example 14 had a pH of 3.65 and an initial viscosity of 3820 cps. The nice smooth texture of the lotion remained through three freeze-thaw cycles and ended with a viscosity of 5340 cps.

Example 15 had a pH of 3.46 and an initial viscosity of 2530 cps. The smooth texture of the lotion remained through three freeze-thaw cycles ending with a final viscosity of 4780 cps. It also showed a viscosity of 6330 cps after aging at 49° C. for four weeks.

Example 16 had a pH of 3.66 and an initial viscosity of 4080 cps. The nice smooth texture of the lotion persisted through three freeze-thaw cycles having a viscosity of 4960 cps at the end. It also showed a viscosity of 5030 cps after aging at 49° C. for four weeks.

It should be noted that the last three Examples all contained isosteareth-2 and isoceteth-20 as emulsifiers. Propylene glycol isoceteth-3 and dipropylene glycol isoceteth-20 acetate may be substituted for these emulsifiers.

It should be known to those skilled in the art that the viscosities shown in the examples are not meant to be absolute values, but are dependent of conditions such as carbon chain distributions of the fatty alcohols, cooling rates and mixing speeds.

It should also be clear to those skilled in the art that the initial viscosity of an emulsion like the above examples may be noticeably lower than the actual viscosity attained after 24 hours.

EXAMPLE 17

Example 17

| Component | Amount |
|---|---|
| Part A | |
| Deionized Water | 49.482 |
| Citric Acid, anhydrous | 0.10 |
| Distearyl Dimonium Chloride | 1.250 |
| Hydroxyethyl Cellulose | 0.250 |
| Propylene Glycol | 0.500 |
| Lactic Acid | 0.300 |
| Part B | |
| Stearyl Alcohol | 1.50 |
| Cetyl Alcohol | 3.000 |
| Stearamidopropyl Dimethylamine | 1.000 |
| Mineral Oil (Heavy, white) | 0.550 |
| Cyclomethicone (Pentamer) | 0.750 |
| Dimethicone, 60,000 cps | 0.550 |
| Dipropylene Glycol Isoceteth-20 Acetate | 0.100 |
| Propylene Glycol Isoceteth-3 Acetate | 0.100 |
| Part C | |
| Deionized Water | 40.000 |
| Part D | |
| Fragrance | Q.S |
| Preservative | Q.S |
| Total | 100.000 |

The pH of this composition was 3.65 and the initial viscosity was 25600 cps.

Although the invention has been described with a certain amount of particularity, it is understood that the present disclosure of the preferred forms has been made only by way of example and the numerous changes and modifications can be made without departing from the spirit and scope of the invention.

What is claimed is:

1. In a hair conditioning aqueous emulsion comprising (a) a quaternary compound, (b) at least one unctous compound and (c) a protective colloid, an improvement in freezing and freezing-thawing properties thereof which comprises incorporating therein a combination of ethoxylated branched-chain fatty alcohol ethers and/or esters as freeze-thaw stabilizers wherein (1) the combination of ethoxylated branched-chain fatty alcohol ethers and/or esters includes ethers and esters having both high and low HLB values; and (2) the high HLB values are in the range of 10.0–19.0 and the low HLB values are in the range of 2.0–9.0, while maintaining the pH of said emulsion in a range of 2.0 to 5.5, and wherein said low HLB ethoxylated alcohol and/or ester have up to eight moles of ethylene oxide and said high HLB ethoxylated alcohol and/or ester have more than nine moles of ethylene oxide.

2. The emulsion claimed in claim 1 wherein the branched-chain fatty alcohols are selected from the group consisting of isocetyl alcohol, isostearyl alcohol, and mixtures of.

3. The emulsion claimed in claim 1 which further includes a surfactant or emulsifier selected from a group consisting of anionic surfactants, amphoteric surfactants, non-ionic surfactants and combinations thereof.

4. The emulsion claimed in claim 1 wherein the pH is in the range of 2.0 to 5.5.

5. The emulsion claimed in claim 1 wherein the quaternary compound comprises one or more cationic quaternay ammonium salts having the formula:

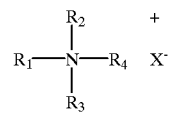

wherein $R_1$, $R_2$, $R_3$ and $R_4$ are each alkyl groups or hydrogen with the proviso that at least one is a higher ($C_{10}$–$C_{22}$) alkyl and X is an anion.

6. The emulsion claimed in claim 5 wherein $R_1$ and $R_2$ are higher ($C_{10}$ to $C_{22}$) alkyl groups, $R_3$ and $R_4$ are each methyl groups and X is chloride or methyl sulfate.

7. The emulsion claimed in claim 1 wherein pH is regulated by the addition of an hydroxy aliphatic acid, or an inorganic acid.

8. The emulsion claimed in claim 7 wherein the hydroxy aliphatic acid is lactic acid.

9. The emulsion claimed in claim 1 wherein the unctous compounds are fatty alcohols, and/or hydrocarbons.

10. The emulsion claimed in claim 1 wherein the protective colloid is a cellulose derivative selected from the group consisting of methyl cellulose, hydroxyethyl cellulose, sodium carboxymethyl cellulose, and hydroxyalkyl methyl celluloses.

11. The emulsion claimed in claim 10 wherein the cellulose derivative is hydroxy ethyl cellulose.

12. The emulsion claimed in claim 1 which contains at least one additional conditioning agent.

13. The emulsion claimed in claim 12 wherein the additional conditioning agent is a polyquaternium polymer.

14. The emulsion claimed in claim 12 wherein the additional conditioning agent is a silicon material.

15. The emulsion claimed in claim 14 wherein the silicon material is selected from the group consisting of dimethicone, cyclomethicone, and mixtures thereof.

16. An emulsion as claimed in claim 5 wherein the quaternary compound is selected from the group consisting of steapyrium chloride, stearalkonium chloride, stearalkonium hectorite, stearamidopropalkonium chloride, steartrimonium chloride, stearyl hydroxyethylimidonium chloride, distearyl dimethyl ammonium chloride, dilauryl dimethyl ammonium chloride, dihydrogenated tallow dimethyl ammonium chloride, dihexadecyl dimethyl ammonium chloride, deteradecyl diethyl ammonium chloride, dicetyl dimethyl ammonium cholride, didicosyl dipropyl ammonium bromide, and dieicosyl diethyl ammonium methyl sulfate.

* * * * *